United States Patent
Kara et al.

(10) Patent No.: US 8,394,937 B2
(45) Date of Patent: Mar. 12, 2013

(54) EXPRESSION SYSTEM

(75) Inventors: Bhupendra Vallabh Kara, Billingham (GB); Ian John Hodgson, Billingham (GB)

(73) Assignee: Fujifilm Diosynth Biotechnologies UK Limited, Billingham (GB)

( * ) Notice: Subject to any disclaimer, the term of this patent is extended or adjusted under 35 U.S.C. 154(b) by 118 days.

(21) Appl. No.: 12/599,529

(22) PCT Filed: May 8, 2008

(86) PCT No.: PCT/GB2008/001597
§ 371 (c)(1),
(2), (4) Date: Nov. 10, 2009

(87) PCT Pub. No.: WO2008/139153
PCT Pub. Date: Nov. 20, 2008

(65) Prior Publication Data
US 2010/0136619 A1    Jun. 3, 2010

(30) Foreign Application Priority Data
May 11, 2007    (GB) .................................. 0709061.6

(51) Int. Cl.
 C07H 21/04    (2006.01)
 C12N 15/70    (2006.01)
 C12N 1/21    (2006.01)
(52) U.S. Cl. ................ 536/23.1; 435/320.1; 435/252.33
(58) Field of Classification Search .......................... None
See application file for complete search history.

(56) References Cited

FOREIGN PATENT DOCUMENTS

| WO | WO 99/05297 | 2/1999 |
|---|---|---|
| WO | WO 2007/088371 | 8/2007 |

OTHER PUBLICATIONS

Alexander et al., Regulated Expression of Foreign Genes in Vaccinia Virus under the Control of Bacteriophage T7 RNA Polymerase and the *Escherichia coli* lac Repressor, Journal of Virology, 66(9):2934-2942 (May 1992).
Lebedeva et al., "A new T7 RNA polymerase-driven expression system induced via thermoamplification of a recombinant plasmid carrying a T7 promoter—*Escherichia coli* lac operator", Gene, 142:61-66 (1994).
Dubendorff et al., "Controlling Basal Expression in an Inducible T7 Expression System by Blocking the Target T7 Promoter with lac Repressor", J. Mol. Biol., 219:45-59 (1991).
Brunschwig et al., "A two-component T7 system for the overexpression of genes in *Pseudomonas aeruginosa*", Gene, 111:35-41 (1992).
Tabor et al., "A bacteriophage T7 RNA polymerase/promoter system for controlled exclusive expression of specific genes", Proc. Natl. Acad. Sci. USA, 82:1074-1078 (Feb. 1985).
Gupta et al., "Enhancing recombinant protein yields in *Escherichia coli* using the T7 system under the control of heat inducible $\lambda P_L$ promoter", Journal of Biotechnology, 68:125-134 (1999).
Simons et al., "Possible ideal lac operator: *Escherichia coli* lac operator-like sequences from eukaryotic genomes lack the central G·C pair", Proc. Natl. Acad. Sci. USA, 81:1624-1628 (Mar. 1984).
Hodgson et al., "Novel systems for rapid fermentation process development of biopharmaceuticals", Journal of Biotechnology, 131(2):S153 (Sep. 2009).
Studier, F.W. et al., "Use of Bacteriophage T7 RNA Polymerase to Direct Selective High-level Expression of Cloned Genes." J. Mol. Biol. 189: 113-130, 1986.

*Primary Examiner* — Nancy T Vogel
(74) *Attorney, Agent, or Firm* — Morgan, Lewis & Bockius LLP

(57) ABSTRACT

A protein expression system is provided. The system comprises:
a) a T7 RNA polymerase-dependent promoter operably linked to an expression cassette for a protein of interest; and
b) an expression cassette for T7 RNA polymerase operably linked to a λpL promoter and at least two perfect palindrome operator sequences.

15 Claims, 1 Drawing Sheet

Shake-flask expression of hTNFα in strains containing T7 RNA polymerase plasmid compared with that from λDE3.
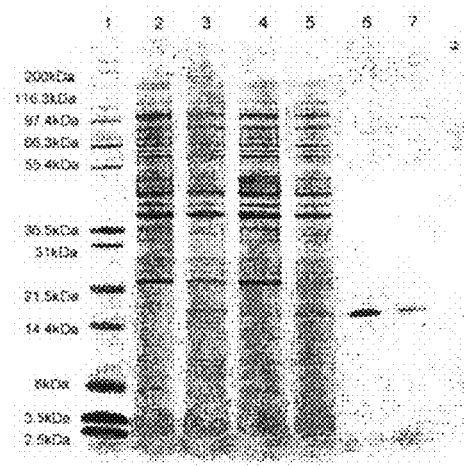
| Lane | Sample |
|------|--------|
| 1 | Molecular weight markers |
| 2 | CLD085 un-induced for 16h |
| 3 | CLD085 induced with 0.5mM IPTG for 3h |
| 4 | CLD086 un-induced for 16h |
| 5 | CLD086 induced with 0.5mM IPTG for 3h |
| 6 | 0.75μg hTNFα reference standard |
| 7 | 0.25μg hTNFα reference standard |

SEQUENCE LISTING

```
<160> NUMBER OF SEQ ID NOS: 6

<210> SEQ ID NO 1
<211> LENGTH: 47
<212> TYPE: DNA
<213> ORGANISM: Artificial Sequence
<220> FEATURE:
<223> OTHER INFORMATION: Oligonucleotide 1 used in preparation of
      Linker 12.1

<400> SEQUENCE: 1
catgtgggaa ttgtgagcgc tcacaattcc aagaacaatc ctgcacg                    47

<210> SEQ ID NO 2
<211> LENGTH: 47
<212> TYPE: DNA
<213> ORGANISM: Artificial Sequence
<220> FEATURE:
<223> OTHER INFORMATION: Synthetic Oligonucleotide 2.1 used in
      preparation of LInker 12.1
```

```
<400> SEQUENCE: 2
aattcgtgca ggattgttct tggaattgtg agcgctcaca attccca                47

<210> SEQ ID NO 3
<211> LENGTH: 78
<212> TYPE: DNA
<213> ORGANISM: Artificial Sequence
<220> FEATURE:
<223> OTHER INFORMATION: Synthetic Oligonucleotide 3 used in preparation
      of pAVE034

<400> SEQUENCE: 3
aattcatctc tggcggtgtt gacataaata ccactggcgg tgatactgag cggaattgtg    60
agcgctcaca attcccca                                                  78

<210> SEQ ID NO 4
<211> LENGTH: 78
<212> TYPE: DNA
<213> ORGANISM: Artificial Sequence
<220> FEATURE:
<223> OTHER INFORMATION: Synthetic Oligonucleotide 4 used in preparation
      of pAVE034

<400> SEQUENCE: 4
ctagtgggga attgtgagcg ctcacaattc cgctcagtat caccgccagt ggtatttatg    60
tcaacaccgc cagagatg                                                  78

<210> SEQ ID NO 5
<211> LENGTH: 30
<212> TYPE: DNA
<213> ORGANISM: Artificial Sequence
<220> FEATURE:
<223> OTHER INFORMATION: Synthetic Primers RNA pol For1

<400> SEQUENCE: 5
taattaatga acacgattaa catcgctaag                                     30

<210> SEQ ID NO 6
<211> LENGTH: 25
<212> TYPE: DNA
<213> ORGANISM: Artificial Sequence
<220> FEATURE:
<223> OTHER INFORMATION: Synthetic Primer RNA pol Back1

<400> SEQUENCE: 6
ggatccttac gcgaacgcga agtcc                                          25
```

EXPRESSION SYSTEM

The present application is a U.S. National Phase Application of International Application PCT/GB2008/001597, filed on May 8, 2008, which claims the benefit of British Patent Application No. 0709061.6, filed on May 11, 2007, which is herein incorporated by reference in their entirety.

The present invention concerns methods and systems for expressing proteins, and specifically methods and systems employing the T7 promoter.

The T7 promoter system is well known for use in the expression of proteins. However, whilst the T7 promoter is recognised as being effective in its ability to express proteins, T7 based systems suffer from certain drawbacks. Operation of the T7 system requires phage polymerase which is commonly provided by inserting a λDE3 prophage expressing the required phage polymerase into the *Escherichia coli* host strain to create lysogenic host strains. The phage polymerase can also be delivered to the cell by infection with a specialised λ transducing phage that carries the gene for the phage polymerase (e.g. T7 RNA polymerase). The λDE3 prophage lacks the genetic elements required for the excision of the prophage to form lytic phage particles. However, λDE3 lysogenic host strains have been shown to release phage particles and thus cause undesirable infections in fermentation plants. Indeed, the use of λDE3 strains is not permitted by certain fermentation plant operators.

Tabor and Richardson (Proc Natl Acad Sci (1985) 82:1074-1078) showed that an operable expression system could be constructed by expressing T7 RNA polymerase from a λPL promoter on one plasmid, and linking a Gene of Interest ("GOI") to the T7 promoter on another plasmid. However, this system gave high uninduced levels of GOI. Mertens et al (Bio/Technology (1995)13:175-179) demonstrated that the system of Tabor and Richardson (supra) as configured is inherently unstable due to the high background expression. The solution they proposed was to add transcription terminators in between the promoter and the T7 RNA polymerase. It was shown that combining this with a temperature inducible λPL promoter led to tight repression. However, this required induction using elevated temperature, which they acknowledged did not allow the flexibility of expression at lower temperatures that may increase product solubility. When an alternative IPTG inducible promoter was used, this was found to give leaky expression, which led to long-term instability. One other problem with systems such as those proposed by Tabor and Richardson, and by Mertens et al, is that when the system is induced then there will be a high level of T7 RNA polymerase expression, which due to its capacity to synthesise large amounts of RNA, which can then be translated into protein, leads to a large metabolic burden on the cell. This places limitations on the use of such systems in fermentation processes, as the induction period can not last very long because the cells stop growing shortly after induction.

There have been a number of reports of alternatives to the lacuv5 promoter, as used in DE3, for expression of T7 RNA polymerase. These include:

a) the use of the arabinose promoter, but this still gives detectable basal levels of expression (see for example, Wycuf (2000) Anal Biochem 277:67-73, Chao et al (2002) Biotechnol Prog 18:394-400);

b) a salt inducible expression system (U.S. Pat. No. 5,830,690), for which there is evidence of instability (Bhandari P and Gowrishankar J. J Bact 1997 179:4403-6);

c) a rhamnose inducible system (Promega Notes (2006) 94:27-30), but this is highly strain specific, and requires high concentrations of an expensive inducer; and d) the gal promoter, which showed a relatively high uninduced level of expression (Menzell and Gramajo (2004) Biotechnol Prog 20:1263-6).

It remains desirable to identify further T7-based expression systems.

According to the present invention, there is provided a protein expression system comprising:

a) a T7 RNA polymerase-dependent promoter operably linked to an expression cassette for a protein of interest; and b) an expression cassette for T7 RNA polymerase operably linked to a λpL promoter and at least two perfect palindrome operator sequences.

T7 RNA polymerase-dependent promoter systems employed in the expression system are preferably single T7 promoters. Examples of such promoters are well known in the art, and include those disclosed by Studier and Moffat, J. Mol. Biol. 189:113-130 (1986), incorporated herein by reference. Most preferably, the T7 RNA polymerase-dependent promoter systems employed is a T7 gene 10 promoter.

Operator sequences which may be employed as perfect palindrome operator sequences in the expression system according to the present invention include lac, gal, deo and gln. In certain embodiments, three or more perfect palindrome operators may be employed, but in many embodiments, dual perfect palindrome operators are employed. In many preferred embodiments, one operator sequence is located downstream of the λpL promoter, and one operator sequence is located upstream of the λpL promoter. The operator sequences are preferably spaced to maximise control of the promoter. In many embodiments, the spacing is from 85 to 150 base pairs apart, preferably from 90 to 126 base pairs apart, and most preferably 91 or 92 base pairs apart. In certain embodiments, an operator sequence overlaps with the transcriptional start point.

T7 RNA polymerase-dependent promoter system is commonly employed under the control of at least one operator sequence, which may be palindromic or non-palindromic. Examples of operator sequences which can be employed are well known in the art and include lac, gal, deo, gln, raf, rha, araC, fru and mel. When two operators are employed to control the T7 RNA polymerase-dependent promoter, the operator sequences are preferably spaced to maximise control of the promoter. In many embodiments, the spacing is from 85 to 150 base pairs apart, preferably from 90 to 126 base pairs apart, and most preferably 91 or 92 base pairs apart. In certain embodiments, an operator sequence overlaps with the transcriptional start point.

In certain embodiments, it is preferred that the operator controlling the T7 RNA polymerase-dependent promoter system is induced by the same inducer as the perfect palindrome operator sequences controlling the λpL promoter. For example, when the λpL promoter is controlled by perfect palindromic lac, gal, deo or gln, the T7 RNA polymerase-dependent promoter system is advantageously controlled by the corresponding perfect palindromic, or non-palindromic, lac, gal, deo or gln operator.

It will be recognised that the operators are commonly employed with an appropriate repressor sequence. Repressor sequences produce repressor protein, for example lacI gene sequence when using the lac operators. Other lac repressor sequences may also be used, for example the lacI$^Q$ sequence can be used to increase the level of lac repressor protein. The repressor sequence may also be provided by the host cell genome or by using an additional compatible plasmid. In many embodiments, the repressor sequence selected for the operators controlling the λpL promoter serve as repressor sequences for the operator sequence controlling the T7 RNA polymerase-dependent promoter.

Either or both of the λpL promoter and the T7 RNA polymerase-dependent promoter of the expression system may be integrated into the host cell genome, but preferably both are comprised within extrachromosomal elements such as plasmids. In many embodiments, the λpL promoter and the T7 RNA polymerase-dependent promoter are located on separate compatible plasmids.

Plasmids or expression vectors comprising the expression system of the present invention can be assembled by methods known in the art. The plasmid typically also comprises one or more of the following: a selectable marker, for example a sequence conferring antibiotic resistance, a cer stability sequence and an expression cassette. The expression system may also incorporate a signal sequence if secretion of the desired protein is required.

Expression may be induced by the addition of an inducer such as isopropyl-β-D-1-thiogalactopyranoside (IPTG), analogues of IPTG such as isobutyl-C-galactoside (IBCG), lactose or melibiose. Other inducers may be used and are described more fully elsewhere (e.g. see The Operon, eds Miller and Renznikoff (1978)). Inducers may be used individually or in combination. The construction of appropriate plasmids or expression vectors will be apparent to the scientist of ordinary skill.

The expression system of the present invention can be employed to express proteins in host cells, and especially in microorganisms. As used herein, "proteins" refers generally to peptides and proteins having more than about 10 amino acids. The host cell may be prokaryotic or eukaryotic. Examples of prokaryotic cells include bacterial cells, for example gram-negative bacterial cells, including *E. coli, Salmonella typhimurium, Serratia marsescens* and *Pseudomonas aeruginosa*, and gram-positive bacterial cells including *Bacillus subtilis*. Examples of eukaryotic cells include yeasts, such as *Pichia pastoris, Saccharomyces cerevisiae, Hansenula polymorpha, Kluyveromyces lactis, Schizosaccharomyces pombe*. Mammalian host cells which can be employed include human cell lines, such as human embryonic kidney and PERC.6 cells; murine cell lines, such as NS0 cells; and particularly hamster cell lines such as baby hamster kidney cells and especially Chinese hamster ovary cells. Other eukaryotic host cells such as those of filamentous fungi, plant, insect, amphibian cells or ovarian species may also be employed. Preferred host cells are bacteria, particularly enterobacteriacae, preferably *E. coli*, and especially B or K12 strains thereof.

Plasmids comprising an expression cassette for T7 RNA-polymerase operably linked to a λpL promoter and at least two perfect palindrome operator sequences form another aspect of the present invention. The plasmids may be autonomously replicating plasmids or integrative plasmids.

The expression system of the present invention is advantageously employed for the manufacture of proteins, especially recombinant proteins, by culturing recombinant cells. For the expression of proteins, it will be recognised that the promoter and operator sequence are operably linked to DNA encoding a protein to be expressed.

Accordingly, the present invention also provides a method for the production of a protein which comprises expressing an expression system comprising
a) a T7 RNA polymerase-dependent promoter operably linked to an expression cassette for a protein of interest; and
b) an expression cassette for T7 RNA polymerase operably linked to a λpL promoter and at least two perfect palindrome operator sequences.

The expression system is expressed by methods well known in the art for the cells employed. Preferred expression methods include culturing the recombinant cells in growth medium, especially by fermentation, and then recovering the expressed protein. The term "growth medium" refers to a nutrient medium used for growing the recombinant cells. In many embodiments, a nutrient solution is employed. Suitable growth media for given recombinant cells are well known in the art.

The present invention is illustrated without limitation by the following examples.

Preparation of pAVE034

The starting vector for the generation of pAVE034 was pZT7#2.0, prepared as described in U.S. Pat. No. 6,537,779. pZT7#2.0 has a pAT153 vector backbone, cer stability sequence, tet A/R, a single native lac operator sequence upstream of the gene of interest and an upstream T4 transcription terminator. A T7A3 promoter and dual perfect palindrome lac operators were cloned into this plasmid using synthetic oligonucleotide linkers by means of the Nco I, EcoR I and Xba I restriction enzyme sites.

Linker 12.1 was prepared by annealing the oligonucleotides 1 and 2.1:

```
Oligonucleotide 1
                                         (Seq ID No. 1)
5'CATGTGGGAATTGTGAGCGCTCACAATTCCAAGAACAATCCTGCACG Oligonucleotide 2.1
                                         (Seq ID No. 2)
5'AATTCGTGCAGGATTGTTCTTGGAATTGTGAGCGCTCACAATTCCCA
```

The linker was then ligated to plasmid pZT7#2.0 and transformed into cloning host strain XL-1 Blue MR (Stratagene) as an Nco I/EcoR I fragment. Initial screening of transformants was by restriction digestion using Nco I. The sequence was confirmed by sequencing. The resultant plasmid was named pAVE012.

A λpL promoter cassette was cloned into pAVE012 by annealing oligonucleotides 3 and 4:

```
Oligonucleotide 3
                                         (Seq ID No. 3)
5'AATTCATCTCTGGCGGTGTTGACATAAATACCACTGGCGGTGATACT

GAGCGGAATTGTGAGCGCTCACAATTCCCCA

Oligonucleotide 4
                                         (Seq ID No. 4)
5'CTAGTGGGGAATTGTGAGCGCTCACAATTCCGCTCAGTATCACCGCCA

GTGGTATTTATGTCAACACCGCCAGAGATG
``` the annealed oligonucleotides being ligated to plasmid pAVE012 and transformed into cloning host strain XL-1 Blue MR (Stratagene) as an Xba I/EcoR I fragment. Initial screening was by restriction digest of plasmid DNA. The sequence was then confirmed by sequencing. The resultant plasmid was named pAVE034.

Construction of pAVE089

The T7 RNA Polymerase gene was cloned from *E. coli* BL21 (λDE3) (Novagen catalogue no. 69450-3 using the Polymerase Chain Reaction (PCR). The oligonucleotide primers used were RNA pol For1:

```
5'TAATTAATGAACACGATTAACATCGCTAAG    (Seq ID No. 5)
``` and RNA pol Back1:

5'GGATCCTTACGCGAACGCGAAGTCC    (Seq ID No. 6)

The cycles steps used were:
1) 94° C. 5 minutes
2) 94° C. 1 minute
3) 63° C. 1 minute
4) 72° C. 1 minute
5) 72° C. 5 minutes Steps 2-4 were repeated 30 times. The resultant PCR product was cloned into a TOPO TA PCR cloning system to become NBH0358-66-1.

NBH0358-66-1 was digested with AseI and BamHI and pAVE034 was digested with NdeI and BamHI, the fragments were ligated together and transformed into XL-1 blue MR (Stratagene). Single colonies of transformed bacteria were isolated from agar plates and grown at 37° C. for 16 hours in 5 mL of Luria Broth (LB) supplemented with tetracycline (10 μg/ml). Initial screening of transformants was by restriction digestion using AfiII. The resultant plasmid was named pAVE089. A positive clone was identified by test for activity using the DE3 Lysogenisation kit supplied by Novagen, Cat No. 69734-3.

Construction of pAVE067 (pACYC-duet/hTNFα).

The human TNFα gene was cloned as an Nde I/Xho I fragment into pACYC-duet digested with Nde I/Xho I. This results in the hTNFα gene being under the control of a T7 promoter. Recombinant plasmids were screened by restriction digest and confirmed by sequencing. The resultant plasmid was named pAVE067.

Construction of CLD085

Plasmids pAVE089 and pAVE067 were co transformed into E. coli host strain BL21 (Novagen catalogue no. 69449-3). Colonies were selected for by plating onto LB agar medium supplemented with tetracycline (10 μg/ml) and chloramphenicol (34 μg/ml). A single colony was picked and grown in LB medium supplemented with tetracycline (10 μg/ml) and chloramphenicol (34 μg/ml). The resultant recombinant strain (CLD085) was maintained in glycerol stocks at −80° C.

Construction of CLD086 (Comparative)

Plasmid pAVE067 was transformed into E. coli host strain BL21 (λDE3) (Novagen catalogue no. 69450-3). Colonies were selected for by plating onto LB supplemented with chloramphenicol (34 μg/ml). The resultant recombinant strain (CLD086) was purified and maintained in glycerol stocks at −80° C. as described above).

Shake-Flask Expression of hTNFα

A vial of each of CLD085 and CLD086 was removed were removed from the −80° C. freezer and allowed to thaw. 10 μl of the thawed glycerol stock was inoculated into 5 ml Luria Broth (LB, 5 g/L yeast extract (Oxoid), 10 g/L tryptone (Oxoid), and 5 g/L sodium chloride) supplemented with chloramphenicol (34 μg/ml) and tetracycline (10 μg/ml) for CLD085 and with choramphenicol only (CLD086). The cultures were incubated at 37° C. in an orbital shaker for 16 h. 500 μl of this culture was then used to inoculate two 250 ml Erlenmeyer flasks containing 50 ml of Luria Broth (composition as described above). The flasks were incubated at 37° C., at 200 rpm in an orbital shaker. Growth was monitored until $OD_{600}$=0.5-0.7. At this point one flask was induced with IPTG (isopropyl-.β.-D-1-thiogalactopyranoside) to a final concentration 0.5 mM whilst the second flask was left uninduced to monitor basal expression. The incubation was continued, under the conditions described above, during which samples were taken for measurement of growth, accumulation of hTNFα within the bacterial cells. The accumulation level of hTNFα was determined using densitometry scanning of Colloidal Blue stained SDS-PAGE gels of whole cell lysates of the sampled bacteria. The results obtained are shown in FIG. 1.

The data shows that delivering T7 RNA polymerase on pAVE089 (CLD085) led to similar levels of human TNFα expression and accumulation as the use of a λDE3 strain (CLD086). Surprisingly, in the absence of induction, the λDE3 strain produced a detectable level of human TNFα, whereas the recombinant using pAVE089 strain did not. This demonstrates that recombinant strains transformed with pAVE089 are less 'leaky' in terms recombinant protein expression in the absence of inducer than those utilising λDE3, whilst being capable of induction to produce the same levels of target protein expression after induction. This is particularly surprising given that CLD085 comprises a multicopy plasmid whereas in CLD086, λDE3 is present as a single copy on the host chromosome.

The invention claimed is:

1. A protein expression system comprising:
   a) a T7 RNA polymerase-dependent promoter operably linked to an expression cassette for a protein of interest; and
   b) an expression cassette for T7 RNA polymerase operably linked to a λpL promoter and at least two perfect palindrome operator sequences.

2. An expression system according to claim 1, wherein the perfect palindrome operator sequences are selected from the group consisting of lac, gal, deo and gln.

3. An expression system according to claim 1 or 2, wherein dual perfect palindrome operator sequences are employed.

4. An expression system according to claim 1, wherein the T7 RNA polymerase-dependent promoter and the expression cassette for T7 RNA polymerase are located on plasmids.

5. An expression system according to claim 4, wherein the T7 RNA polymerase-dependent promoter and the expression cassette for T7 RNA polymerase are located on separate compatible plasmids.

6. A method for the production of a protein which comprises expressing an expression system according to claim 1.

7. A method according to claim 6, wherein the expression occurs in an *E. coli* host cell.

8. A plasmid comprising an expression cassette for T7 RNA-polymerase operably linked to a λpL promoter and at least two perfect palindrome operator sequences.

9. A host cell transformed with a plasmid according to claim 8.

10. A host cell according to claim 9, wherein the host is *E. coli*.

11. A host cell according to claim 10, wherein the host is *E. coli* strain B or strain K12.

12. An expression system according to claim 4, wherein the perfect palindrome operator sequences are selected from the group consisting of lac, gal, deo and gln.

13. An expression system according to claim 12, wherein dual perfect palindrome operator sequences are employed.

14. The method of claim 7, wherein the *E. coli* host cell is a B strain.

15. The method of claim 7, wherein the *E. coli* host cell is a K12 strain.

* * * * *